(12) United States Patent
Nan et al.

(10) Patent No.: US 8,247,549 B2
(45) Date of Patent: Aug. 21, 2012

(54) METHOD FOR PREPARING 4-(6-AMINO-PURIN-9-YL)-2(S)-HYDROXY-BUTYRIC ACID METHYL ESTER

(75) Inventors: Fajun Nan, Shanghai (CN); Jianping Zuo, Shanghai (CN); Yangming Zhang, Shanghai (CN); Min Gu, Shanghai (CN); Wei Tang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 12/747,312

(22) PCT Filed: Nov. 6, 2008

(86) PCT No.: PCT/CN2008/001852
§ 371 (c)(1),
(2), (4) Date: Sep. 7, 2010

(87) PCT Pub. No.: WO2009/079907
PCT Pub. Date: Jul. 2, 2009

(65) Prior Publication Data
US 2011/0201810 A1    Aug. 18, 2011

(30) Foreign Application Priority Data
Dec. 10, 2007  (CN) .......................... 2007 1 172019

(51) Int. Cl.
*C07D 473/34* (2006.01)
(52) U.S. Cl. ...................................... 544/277
(58) Field of Classification Search .................. None
See application file for complete search history.

(56) References Cited

FOREIGN PATENT DOCUMENTS
GB          1330704 A         9/1973

OTHER PUBLICATIONS

Zhang et al., Bioorg. Med. Chem, 16 (2008) 9212-9216.*
"Synthesis and biological evaluation of immunosuppressive agent DZ2002 and its stereoisomers" by Yang-Ming Zhang et al., Published by Elsevier Ltd. in the Bioorganic & Medicinal Chemistry, vol. 16, No. 20, Oct. 15, 2008; ISSN 0968-0896; pp. 9213-9216.
H. Kim et al., "Malic Acid: A Convenient Precursor for the Synthesis of Peptide Secondary Structure Mimetics," Tetrahedron Letters, vol. 38, No. 28, Jul. 14, 1997, pp. 4935-4938.
K. Augustyns et al., "Influence of the Incorporation of (S)-9-(3,4-Dihydroxy-Butyl)Adenine on the Enzymatic Stability and Base-Pairing Properties of Oligodeoxynucleotides," Nucleic Acids Research, vol. 19, No. 10, May 25, 1991, pp. 2587-2593.
Supplementary European Search Report, Appl. No. EP 08864601, dated Aug. 29, 2011.

* cited by examiner

*Primary Examiner* — Sun Jae Loewe
(74) *Attorney, Agent, or Firm* — Baker & Hostetler LLP

(57) ABSTRACT

The present invention discloses a novel method for preparing and purifying 4-(6-Amino-purin-9-yl)-2(S)-hydroxy-butyric acid methyl ester. The preparation started from cheap and easily available L-malic acid, which was transformed to intermediate I after simultaneous protection of the groups of 1-carboxyl and 2-hydroxyl. The intermediate I was selectively reduced to intermediate alcohol II, whose hydroxyl group was further transformed to an easily leaving group to afford intermediate III. The intermediate III was nucleophilically substituted with adenine to afford intermediate IV. The intermediate IV was deprotected and methyl-esterified simultaneously in methanol in the presence of an acid or a base to afford crude 4-(6-Amino-purin-9-yl)-2(S)-hydroxy-butyric acid methyl ester, which was purified by recrystallization to afford the purified product. Comparing with the prior preparation methods, the present method has advantages in low cost, mild conditions, high retention of the chiral center during the reaction, high productivity, great improvement in the quality and yield of the product and great decrease in cost, and thus is suitable for the production on a large scale.

11 Claims, No Drawings

METHOD FOR PREPARING 4-(6-AMINO-PURIN-9-YL)-2(S)-HYDROXY-BUTYRIC ACID METHYL ESTER

CROSS-REFERENCE TO RELATED APPLICATIONS

This application is a National Stage of International patent application PCT/CN2008/001852, filed on Nov. 6, 2008, which claims priority to foreign patent application CN 200710172019.4, filed on Dec. 10, 2007.

FIELD OF THE INVENTION

The present invention generally relates to the fields of pharmaceutical chemistry. More particularly, the present invention relates to a novel method for preparing and purifying 4-(6-Amino-purin-9-yl)-2(S)-hydroxy-butyric acid methyl ester (hereinafter, referred to as DZ2002).

BACKGROUND OF THE INVENTION

DZ2002 is a reversible inhibitor of S-Adenosyl-L-homocysteine hydrolase (SAHH). It has been demonstrated that DZ2002 selectively suppresses macrophage function and activates B cells function, inhibits cell immune and humoral immune responses, and has a wide margin between the toxic and therapeutic doses with a high therapeutic index (Chong-Sheng Yuan, USP: 2005/0182075, 2005; Yun-Feng Fu, Jun-Xia Wang, Jian-Ping Zuo etc., *The Journal of Pharmacology and Experimental Therapeutics*, 118, 1229~1237; Brian R. Lawson, Yulia Manenkova, Chong Yuan etc., *The Journal of Immunology*, 178, 5366~5374, 2007).

A known method for preparing DZ2002 started from (S)-(−)-α-hydroxybutyrolactone, after the hydroxyl group had been protected with a silyl group, the lactone was treated with tetraisopropyl titanate to open the lactone ring, followed by being converted to a corresponding p-toluenesulfonate. Then it was nucleophilically substituted with adenine and deprotected by removal of the silyl protective group to obtain DZ2002. The details are shown in Scheme 1. In the preparation method, (S)-(−)-α-hydroxybutyrolactone is expensive, the ring-opening reaction using tetraisopropyl titanate has a low yield with a complicated post-treatment, and the chiral center tends to be racemized during the reaction. In addition, DZ2002 is purified by column chromatography, which is time-consuming with a low productivity.

Scheme 1

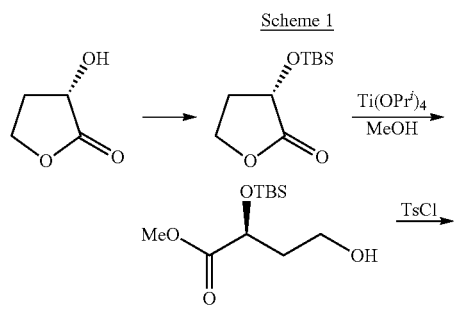

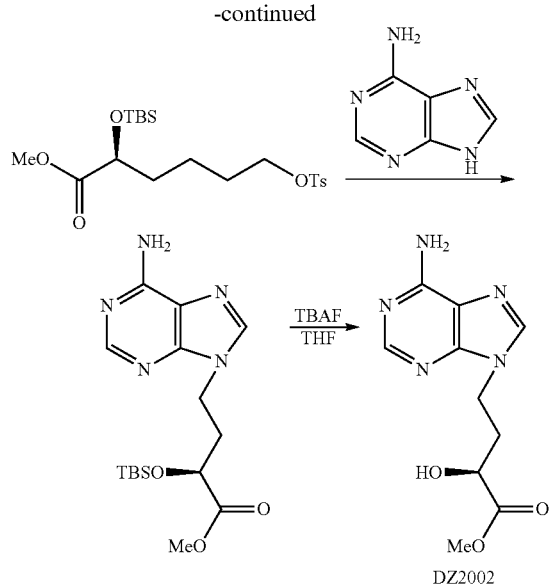

SUMMARY OF THE INVENTION

The present invention aims at developing an effective method for preparing and purifying DZ2002 on a large scale, which utilizes L-malic acid as a starting material. The present invention has advantages in easily available materials, low cost, simple operation process, high productivity, easily being scaled-up, as well as high retention of the chiral center during the reaction.

The object of the present invention was achieved by a process illustrated in Scheme 2.

Scheme 2

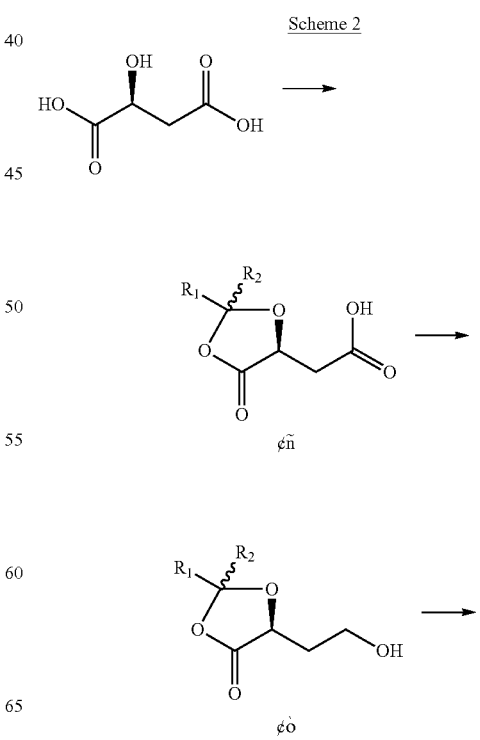

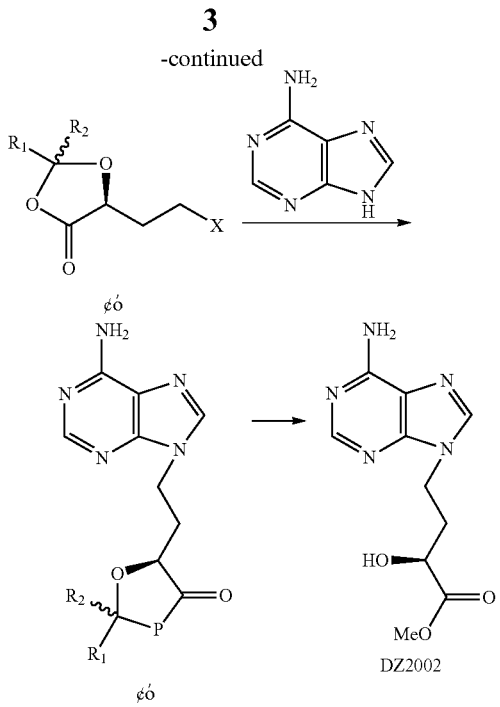

The present invention provides a method for preparing 4-(6-Amino-purin-9-yl)-2(S)-hydroxy-butyric acid methyl ester, comprising the following steps.

(1) A ring-closing reaction was carried out by a nucleophilic substitution between L-malic acid and a protective agent, a carbonyl compound having a structure of $R_1COR_2$ or a diol-carbonyl condensation compound thereof, to selectively give an intermediate I whose 1-carboxyl and 2-hydroxyl groups were both protected simultaneously, wherein $R_1$ and $R_2$ are each independently H, methyl, ethyl, n-propyl, n-butyl, phenyl, p-methoxyphenyl or the like. The carbonyl compound is preferably acetone, and the diol-carbonyl condensation compound is preferably acetone dimethyl acetal. In this case, $R_1=R_2=$methyl.

The intermediate I, whose 1-carboxyl and 2-hydroxyl groups are both protected selectively, may be easily obtained by reacting L-malic acid with the protective agent in an appropriate solvent in the presence of a weak acid as a catalyst. With respect to the kind of the protective group and the corresponding incorporation process thereof, reference is made to "*Protective groups in organic synthesis*" (The organic chemistry teaching and researching group of East China University of Science and Technology (translated), East China University of Science and Technology Press, 2004).

(2) The intermediate I obtained from step (1) was reduced to an intermediate alcohol II by a reducing agent, wherein the 4-carboxyl group of the intermediate I was reduced to the corresponding hydroxyl group by a reducing agent such as a borane agent or a metal hydride to give the intermediate alcohol II. The borane agent may be borane, borane-pyridine complex, borane-dimethylthioether complex, borane-tetrahydrofuran complex, borane-ammonia complex or the like. The metal hydride may be $LiAlH_4$, $NaBH_4$, $KBH_4$ or $NaBH_3CN$. In the case of when the reducing agent is a metal hydride, it may be used alone or in combination with a reagent selected from the group consisting of $AlCl_3$, $NiCl_2$, $CeCl_3$, $ZnCl_2$, LiCl, $I_2$ and the like. The reducing agent is preferably a borane or a complex thereof, which may be produced in situ, or a commercially available agent, and more preferably, a commercial borane-dimethylthioether complex.

(3) The intermediate alcohol II obtained from step (2) may be esterified by an acyl chloride selected from the group consisting of p-toluenesulfochloride, mesyl chloride, trifluoro-acetyl chloride, trichloro-acetyl chloride and acetyl chloride in the presence of a base to give an intermediate III, wherein X is one selected from the group consisting of mesyloxyl, p-toluenesulfonyloxyl, trifluoroacetyloxyl, trichloroacetyloxyl and acetyloxyl. Alternatively, the intermediate alcohol II may be halogenated by a halogenating agent selected from the group consisting of phosphorus tribromide, phosphorus pentabromide, carbon tetrabromide/triphenylphosphine and iodine/triphenylphosphine to give an intermediate III, wherein X is Br or I.

More specifically, the hydroxyl of intermediate alcohol II, which was obtained by reduction, was further transformed to a corresponding group that is easy to be removed to give the intermediate III, wherein X is either a substituent such as Br, I and the like, or a corresponding activated ester group such as mesyloxyl, p-toluenesulfonyloxyl, trifluoroacetyloxyl, trichloroacetyloxyl, acetyloxyl and the like, preferably mesyloxyl or p-toluenesulfonyloxyl. When the hydroxyl of the intermediate alcohol II was converted to an activated ester group, the used base is one organic base selected from the group consisting of triethylamine, diisopropylethylamine, pyridine and the like.

(4) The intermediate III obtained from step (3) was nucleophilically substituted by adenine in an appropriate solvent at a suitable temperature in the presence of a base and a phase transfer catalyst to give an intermediate IV.

More specifically, the substitution may be carried out at a temperature in the range of 30° C. to 120° C., preferably 40° C. to 60° C. The phase transfer catalyst may be tetrabutylammonium bromide, tetrabutylammonium chloride, tetrabutylammonium iodide, 18-crown-6, polyethylene glycol or the like, preferably 18-crown-6. The base may be an inorganic base such as sodium hydride, $K_2CO_3$, $Na_2CO_3$, $LiCO_3$, NaOH, KOH, LiOH and the like, or an organic base such as triethylamine, diisopropylethylamine, pyridine, methylpyridine, n-butyllithium, sec-butyllithium, lithium diisopropylamine, lithium hexamethyldisilazide, sodium hexamethyldisilazide, potassium hexamethyldisilazide or the like, preferably sodium hydride, $K_2CO_3$ or $Na_2CO_3$. The solvent may be one selected from a group consisting of a strongly polar non-protonic solvent such as formamide, DMF, DMA, sulfolane, DMSO, NMP, HMPA(hexamethyl phosphoric triamide) and the like; a ketone solvent such as acetone, butanone and the like; an aromatic solvent such as benzene, toluene and the like; an ester solvent such as ethyl acetate, butyl acetate and the like; a chlorohydrocarbon solvent such as dichloromethane, dichloroethane and the like; and a ether solvent such as diisopropyl ether, tetrahydrofuran, dioxane and the like, preferably formamide, DMF, DMA, NMP or sulfolane.

(5) The intermediate IV obtained from step (4) was deprotected and methyl-esterified simultaneously in a methanol system in the presence of an acid or a base to give a crude DZ2002.

The transformation in this step was carried out in a HCl/methanol mixture or sodium alkoxide/methanol mixture, preferably in HCl/methanol mixture. With respect to the process for deprotection, reference is made to "*Protective groups in organic synthesis*" (The organic chemistry teaching and research group of East China University of Science and Technology(translated), East China University of Science and Technology Press, 2004).

In the preparation method according to the present invention, the steps (3) and (4) may be replaced by the following step, that is, the intermediate alcohol II, which was obtained by the selective reduction of step (2), may be directly reacted with adenine through Mitsunobu reaction in the presence of a phosphine agent and a reagent such as diethyl azodiformate (DEAD), diisopropyl azodiformate (DIAD) or the like to give an intermediate IV, the product of the nucleophilic substitution, wherein the phosphine agent is triphenylphosphine or trialkylphosphine, wherein the alkyl is a short chain C1-C4 alkyl.

The resultant crude DZ2002 from the above methods may be purified by recrystallization. The recrystallization may be performed using an alcohol solvent such as methanol, ethanol, isopropanol and the like, or simply using water, or using a mixture of alcohol and water. It is preferable to use water as the solvent for recrystallization.

Racemic DZ2002 can also be synthesized through the present method using a racemic malic acid as a starting material. The racemoid is esterified by a chiral acid such as Mosher agent to give the corresponding ester. The diastereoisomers may be separated through a method such as recrystallization due to their difference in physical properties such as solubility, followed by hydrolysis to give DZ2002. Therefore, the present invention also includes such method.

The present invention has the following significant advantages over the preparation methods of the prior art:

1. In the prior art, (5)-(−)-α-hydroxybutyrolactone was used as a starting material, which is expensive (1788 RMB/g, Aldrich, 2007-2008), while the present invention starts with L-malic acid, which is cheap (30 RMB/kg) and easily available, thus greatly reducing the cost;

2. In the preparation method according to the present invention, the racemization does not tend to occur since the chiral center was protected by ring-formation during the reaction, and thus the product quality is much better than that of the prior art. For example, the product of the prior art has a specific rotation of +12.5° as measured, while DZ2002 prepared by the method of the present invention has a specific rotation which can be generally controlled in the range of +18° to +20°.

3. The method of the present invention has a high productivity and is easily scaled up, since the crude DZ2002 may be purified through recrystallization.

DETAILED DESCRIPTION

Best Mode for Carrying Out the Invention

The present invention will be further illustrated by the following examples, which may not be construed to restrict the scope of the present invention.

I. Selective Protection of L-Malic Acid

Example 1

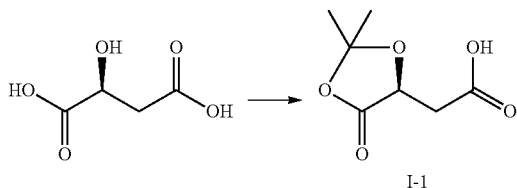

To a suspension of L-malic acid (4.0 g, 30.0 mmol) (SHANG HAI BANGCHENG CHEMICAL Co. Ltd.) in dry acetone (100 ml), p-toluenesulfonic acid (60.0 mg, 0.33 mmol) was added. The mixture was heated to reflux for 6 h to gradually become clear. After the solvent was removed through concentration, the resultant residue was diluted with water (100 ml) and sufficiently extracted with dichloromethane. The combined organic phase was washed with saturated saline, dried and concentrated to obtain a nearly colorless transparent oil, which was then recrystallized from dichloromethane/n-hexane (1/5, v/v), dried in vacuo to afford compound I-1 (2.0 g) as a white crystal with a yield of 50.0%.

Example 2

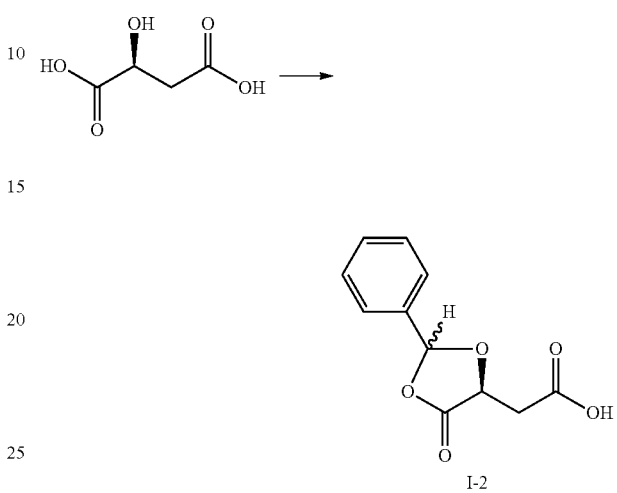

To a suspension of L-malic acid (4.0 g, 30.0 mmol) in dry benzene (80 ml), were added fresh phenyl aldehyde (3.2 g, 30 mmol) and pyridinium p-toluenesulfonate (151.0 mg, 0.6 mmol). After heated to reflux and water-segregated for 3 h, the mixture became clear. After the solvent was removed through concentration, the resultant residue was diluted with water (100 ml) and sufficiently extracted with dichloromethane. The combined organic phase was washed with saturated saline, dried and concentrated to afford compound I-2 (4.3 g) as a nearly colorless transparent oil with a yield of 65.3%, which will be used directly in the next step without purification.

Example 3

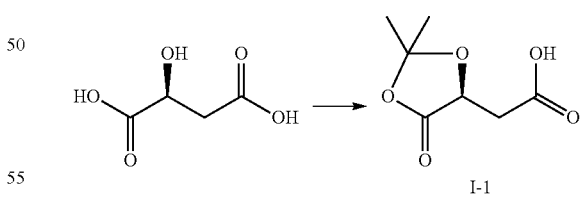

To a suspension of L-malic acid (10.0 g, 74.6 mmol) in fresh 2,2-dimethoxypropane (100 ml), p-toluenesulfonic acid (0.20 g, 1.04 mmol) was added. After reacted at room temperature for 3 h, the mixture became clear. After the solvent was removed through concentrating, the resultant residue was diluted with water (150 ml) and sufficiently extracted with dichloromethane. The combined organic phase was washed with saturated saline, dried and concentrated to obtain a nearly colorless transparent oil, which was then slowly solidified to afford compound I-1 (4.8 g) as a white crystal with a yield of 37.0%.

Example 4

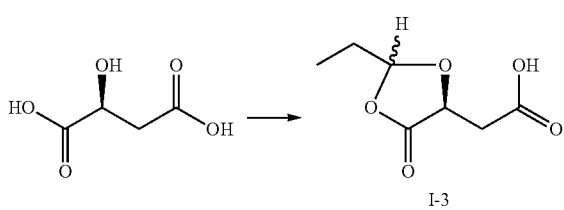

I-3

To a suspension of L-malic acid (6.7 g, 50.0 mmol) in fresh ethyl ether (100 ml), redistilled propylaldehyde (3.2 g, 55.0 mmol) was added under ice bath. Redistilled boron trifluoride etherate (19.0 ml, 150.0 mmol) was then added dropwise for 30 min, followed by keeping the temperature for 3 h. After diluted with water (100 ml), the mixture was sufficiently extracted with ethyl ether. The combined organic phase was washed with saturated saline, dried and concentrated to afford compound I-3 (6.8 g) as a nearly colorless transparent oil with a yield of 78.1%, which will be used directly in the next step without purification.

II. Selective Reduction of the Protected L-Malic Aid, Intermediate I, to Alcohol II (Illustrated with the Case that $R_1=R_2$=Methyl, i.e., Compound I-1, which may not be Construed to Restrict the Invention)

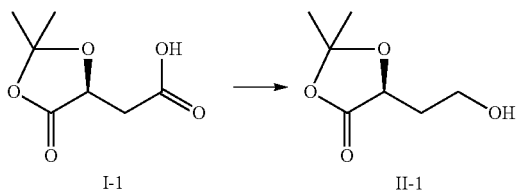

I-1     II-1

Example 1

To a solution of the compound I-1 (24.4 g, 0.14 mol) obtained from the last step in fresh tetrahydrofuran (150 ml), was dropwise added a solution (2M, 77.0 ml, 0.15 mol) of borane-methyl sulfide complex in tetrahydrofuran for 1.5 h under ice bath. After the addition, the mixture was stirred at that temperature for 2 h and then at room temperature for 12 h. Methanol (77.0 ml) was slowly and dropwise added into the mixture to destroy the residual borane. After the addition, the mixture was stirred at room temperature for 30 min, and then concentrated. The resultant residue was purified through silica-gel column chromatography eluting with n-hexane/ethyl acetate (2/1, v/v) to afford alcohol II-1 with a yield of 74.1-86.6%.

Example 2

To a suspension of sodium borohydride (6.4 g, 0.17 mol) in tetrahydrofuran (50 ml), was dropwise added a solution of the resultant compound I-1 (24.4 g, 0.14 mol) from the last step in fresh tetrahydrofuran (50 ml) for 1 h under room temperature. After the addition, a solution of iodine (21.6 g, 0.085 mol) in tetrahydrofuran (50 ml) was dropwise added to the above mixture for 1 h, followed by stirring for 2 h at room temperature. After methanol (50 ml) was slowly and dropwise added into the reaction system, the mixture was stirred at room temperature for 30 min, and then concentrated. The resultant residue was purified through silica-gel column chromatography eluting with n-hexane/ethyl acetate (2/1, v/v) to afford alcohol II-1 with a yield of 62.1-75.0%.

Example 3

To a suspension of sodium borohydride (7.2 g, 0.19 mol) in tetrahydrofuran (100 ml), was dropwise added a fresh boron trifluoride etherate (26.8 g, 0.19 mol) for 1.5 h under ice bath, generating a large amount of gas and white turbidness. After removing the ice bath, the mixture was stirred at room temperature for 1 h. A solution of the compound I-1 (24.4 g, 0.14 mol) obtained from the last step in tetrahydrofuran (50 ml) was dropwise added for 1.5 h under ice bath, followed by stirring for 12 h at room temperature. After methanol (70 ml) was slowly and dropwise added into the reaction system, the mixture was stirred at room temperature for 30 min, and then concentrated. The resultant residue was purified through silica-gel column chromatography eluting with n-hexane/ethyl acetate (2/1, v/v) to afford alcohol II-1 with a yield of 55.0-65.3%.

Example 4

To a suspension of sodium borohydride (7.2 g, 0.19 mol) and fresh dimethyl sulfide (11.8 g, 0.19 mol) in tetrahydrofuran (100 ml), was dropwise added a fresh boron trifluoride esterate (26.8 g, 0.19 mol) for 1.5 h under ice bath, generating a large amount of gas and white turbidness. After removing the ice bath, the mixture was stirred at room temperature for 1 h. A solution of the compound I-1 (24.4 g, 0.14 mol) obtained from the last step in tetrahydrofuran (50 ml) was dropwise added for 1.5 h under ice bath, followed by stirring for 12 h at room temperature. After methanol (70 ml) was slowly and dropwise added into the reaction system, the mixture was stirred at room temperature for 30 min, and then concentrated. The resultant residue was purified through silica-gel column chromatography eluting with n-hexane/ethyl acetate (2/1, v/v) to afford alcohol II-1 with a yield of 71.2-85.6%.

Example 5

To a suspension of sodium borohydride (7.2 g, 0.19 mol) and fresh dimethyl sulfide (11.8 g, 0.19 mol) in tetrahydrofuran (100 ml), was dropwise added a solution of fresh trimethylsilyl chloride (20.6 g, 0.19 mol) in tetrahydrofuran (50 ml) for 1.5 h under ice bath, generating a large amount of gas and white turbidness. After removing the ice bath, the mixture was stirred at room temperature for 1 h. A solution of the compound I-1 (24.4 g, 0.14 mol) obtained from the last step in tetrahydrofuran (50 ml) was dropwise added for 1.5 h under ice bath, followed by stirring for 12 h at room temperature. After methanol (70 ml) was slowly and dropwise added into the reaction system, the mixture was stirred at room temperature for 30 min, and then concentrated. The resultant residue was purified through silica-gel column chromatography eluting with n-hexane/ethyl acetate (2/1, v/v) to afford alcohol II-1 with a yield of 78.2-83.5%.

III. Transformation of the Intermediate Alcohol II to Intermediate III (Illustrated by Alcohol II-1, which may not be Construed to Restrict the Invention)

Example 1

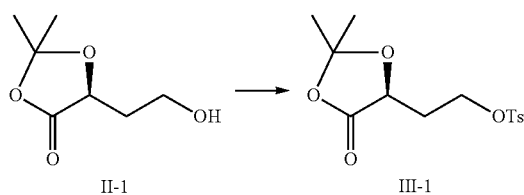

II-1    III-1

To a solution of the alcohol II-1 (52.8 g, 0.33 mol) obtained from the last step in fresh pyridine (250 ml), p-toluenesulfonyl chloride (62.7 g, 0.33 mol) was batchwise added under ice bath, followed by stirring at room temperature for 5 h. After the solvent was recovered under reduced pressure, the resultant residue was diluted with ethyl acetate (400 ml), washed with HCl solution (5%), saturated sodium bicarbonate solution and saline respectively, dried and concentrated. The resultant residue was purified through silica-gel column chromatography eluting with n-hexane/ethyl acetate (10/1, v/v) to afford intermediate III-1 with a yield of 59.8-67.6%.

Example 2

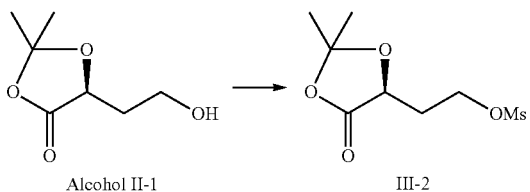

Alcohol II-1    III-2

To a solution of the alcohol II-1 (32.0 g, 0.20 mol) obtained from the last step and N,N-diisopropylethylamine (51.6 g, 0.40 mol) in fresh dichloromethane (200 ml), fresh mesyl chloride (22.8 g, 0.20 mol) was dropwise added for 30 min under ice bath, followed by stirring at room temperature for 3 h. After the solvent was recovered under reduced pressure, the resultant residue was diluted with ethyl acetate (400 ml), washed with HCl solution (5%), saturated sodium bicarbonate solution and saline respectively, dried and concentrated. The resultant residue was purified through silica-gel column chromatography eluting with n-hexane/ethyl acetate (10/1, v/v) to afford intermediate 111-2 with a yield of 71.2-77.7%.

Example 3

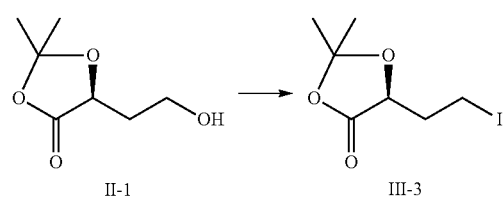

II-1    III-3

To a solution of iodine (57.2 g, 0.23 mol) in dichloromethane (300 ml), triphenylphosphine (59.0 g, 0.23 mol) was batchwise added at room temperature. After stirring for 15 min, imidazole (25.5 g, 0.38 mol) was added thereto, and the stirring continued for 15 min. A solution of the alcohol II-1 (24.0 g, 0.15 mol) in dichloromethane (100 ml) was then dropwise added into the above reaction system, and the mixture was stirred at room temperature for 12 h. After the mixture was concentrated, the residue was sufficiently extracted with methyl tert-butyl ether, followed by concentrating the extract. The residue was purified through silica-gel column chromatography eluting with n-hexane/ethyl acetate (10/1, v/v) to afford intermediate III-3 with a yield of 65.6-78.3%.

Example 4

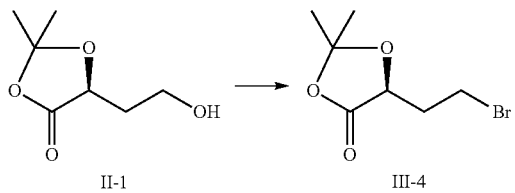

II-1    III-4

To a solution of the alcohol II-1 (25.6 g, 0.16 mol) obtained from the last step in fresh dichloromethane (250 ml), carbon tetrabromide (68.2, 0.21 mol) was added batchwise. A solution of triphenylphosphine (55.0 g, 0.21 mol) in dichloromethane (200 ml) was then charged dropwise into the reaction system for 1 h under ice bath, followed by stirring at room temperature for 12 h. After the mixture was concentrated, the residue was sufficiently extracted with methyl tert-butyl ether, followed by concentrating the extract. The residue was purified through silica-gel column chromatography eluting with n-hexane/ethyl acetate (10/1, v/v) to afford the corresponding intermediate III-4 with a yield of 60.2-73.3%.

IV. Nucleophilic Substitution Between Adenine and Intermediate III (Illustrated by Compound III-1, which may not be Construed to Restrict the Invention)

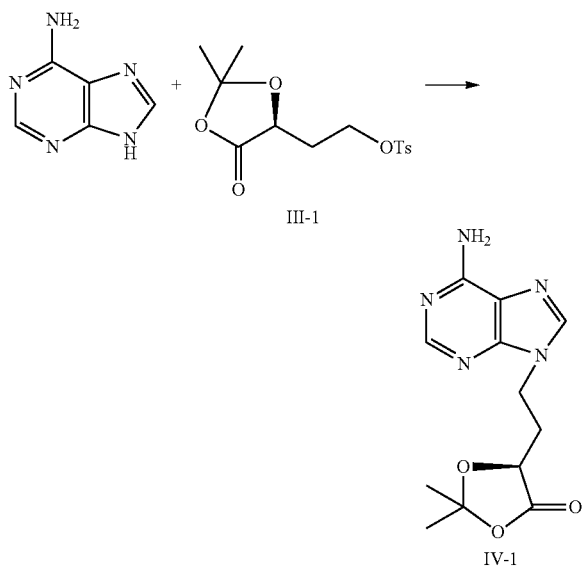

III-1

IV-1

Example 1

To a solution of adenine (47.0 g, 0.35 mol) and 18-crown-6 (1.2 g, 4.5 mmol) in fresh DMF (250 ml), sodium hydride (60%, 14.0 g, 0.35 mol) was batchwise added at room temperature. After the addition, the mixture was stirred at 60° C. for 2 h. A solution of the compound III-1 (53.4 g, 0.17 mol)

obtained from the last step in fresh DMF (50 ml) was dropwise charged into the above mixture at 60° C., and the temperature was kept for 12 h. Under ice bath, the mixture was diluted with water (300 ml), and extracted sufficiently with ethyl acetate. The combined organic phase was washed with saturated saline, dried and concentrated. The resultant residue was purified through silica-gel column chromatography eluting with chloroform/methanol (20:1, v/v, then 10:1, v/v) to afford an intermediate IV-1 with a yield of 29.2-35.3%.

Example 2

To a solution of adenine (47.0 g, 0.35 mol) and 18-crown-6 (1.2 g, 4.5 mmol) in fresh formamide (250 ml), sodium hydride (60%, 14.0 g, 0.35 mol) was batchwise added at room temperature. After the addition, the mixture was stirred at 50° C. for 2 h. A solution of the compound III-1 (53.4 g, 0.17 mol) obtained from the last step in fresh dioxane (50 ml) was dropwise charged into the above mixture at 50° C., and the temperature was kept for 12 h. After the solvent was removed under reduced pressure, the resultant residue was purified through silica-gel column chromatography eluting with chloroform/methanol (20:1, v/v, then 10:1, v/v) to afford the corresponding intermediate IV-1 with a yield of 55.3-59.4%.

Example 3

Adenine (39.2 g, 0.29 mol), intermediate III-1 (44.0 g, 0.14 mol), anhydrous potassium carbonate (60.0 g, 0.44 mol) and 18-crown-6 (1.0 g, 3.8 mmol) were suspended in fresh DMF (220 ml), and the mixture was stirred at 50° C. for 12 h. After the solvent was removed under reduced pressure, the resultant residue was directly purified through silica-gel column chromatography eluting with chloroform/methanol (20:1, v/v, then 10:1, v/v) to afford the intermediate IV-1 with a yield of 44.3-55.0%.

Example 4

Adenine (39.2 g, 0.29 mol), intermediate III-1 (44.0 g, 0.14 mol), anhydrous potassium carbonate (60.0 g, 0.44 mol) and 18-crown-6 (1.0 g, 3.8 mmol) were suspended in fresh DMF (220 ml), and the mixture was stirred at 50° C. for 12 h. Under ice bath, the mixture was diluted with water (300 ml), and extracted sufficiently with ethyl acetate. The combined organic phase was washed with saturated saline, dried and concentrated. The resultant residue was directly purified through silica-gel column chromatography eluting with chloroform/methanol (20:1, v/v, then 10:1, v/v) to afford the corresponding intermediate IV-1 with a yield of 40.1-51.0%.

V. Preparation of Intermediate IV-1 through Mitsunobu Reaction (Illustrated by Compound II-1, which may not be Construed to Restrict the Invention)

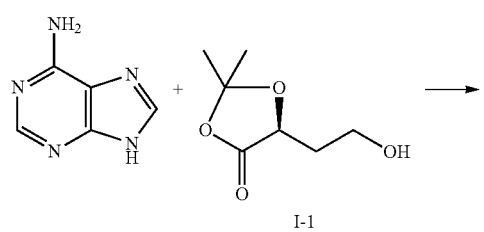

I-1

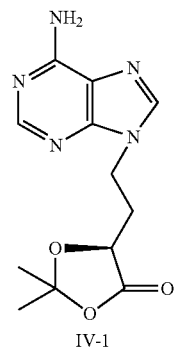

IV-1

Example

To a solution of adenine (7.8 g, 0.058 mol), intermediate II-1 (4.5 g, 0.028 mol) and triphenylphosphine (8.8 g, 0.034 mol) in fresh DMF (50 ml), diethyl azodiformate (DEAD) (5.8 g, 0.034 mol) was charged dropwise at room temperature. After the addition, the mixture was stirred at room temperature for 12 h. Under ice bath, the mixture was diluted with water (50 ml), and extracted sufficiently with ethyl acetate. The combined organic phase was washed with saturated saline, dried and concentrated. The resultant residue was directly purified through silica-gel column chromatography eluting with chloroform/methanol (20:1, v/v, then 10:1, v/v) to afford the intermediate IV-1 with a yield of 38.0-47.2%.

VI Synthesis of Crude DZ2002 (Illustrated with the case that $R_1=R_2=$Methyl, which may not be Construed to Restrict the Invention)

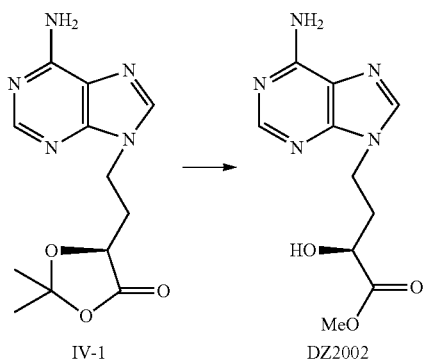

IV-1     DZ2002

Example 1

To a solution of the intermediate IV-1 (18.0 g, 0.065 mol) in 540 ml of methanol, a HCl/methanol solution (0.1 mol) was added dropwise for 30 min under stirring and ice bath. After the addition, the ice bath was removed, and the mixture was stirred at room temperature for 5 h. The completeness of the reaction was identified by TLC (chloroform/methanol=10/1, v/v). After the addition of an appropriate amount of silica-gel, the reaction mixture was concentrated under reduced pressure. The obtained solid was transferred to a silica-gel column in a manner of dry sample and eluted with chloroform/methanol (10/v, v/v, then 5:1, v/v). The eluent containing DZ2002 was concentrated to afford the crude DZ2002 as a light yellow solid with a yield of 51.8-72.5%.

Example 2

To a solution of the intermediate IV-1 (18.0 g, 0.065 mol) in 540 ml of methanol, solid sodium methoxide (7 g, 0.13 mol) was added batchwise for 30 min under stirring and ice bath. After the addition, the ice bath was removed, and the mixture was stirred at room temperature for 3 h. The completeness of the reaction was identified by TLC (chloroform/methanol=10/1, v/v) and the post-treatment was the same as that of the above Example 1. Yield: 40.2-68.7%.

VII. Recrystallization of the Crude DZ2002

Example 1

The above crude DZ2002 (10 g) was suspended in anhydrous methanol (50 ml) and heated to dissolve completely, followed by addition of activated carbon (1 g). After the heating and stirring continued for 30 min, the mixture was hot-filtered and the solid was washed with a small amount of hot methanol. The obtained filtrate was concentrated under reduced pressure, and a solid was precipitated gradually during the concentration. When the volume of methanol was reduced to ⅓ of the original, anhydrous ethyl ether (50 ml) was charged into the concentrate. After stirred at room temperature for 30 min, the mixture was filtered, and the obtained solid was washed with anhydrous ethyl ether and dried in vacuo to afford a nearly white crystal (8.2 g). $^1$HNMR (DMSO-d$^6$): 1.97-2.09(1H, m), 2.17-2.26(1H, m), 3.57 (3H, s), 3.96-4.03(1H, m), 4.20-4.25(2H, t), 5.68-5.70(1H, d), 7.16 (2H, s), 8.05(1H, s), 8.12(1H, s). LC purity: no less than 99.5%; Single impurity: no more than 0.2%; Specific rotation: +18°-+20°; Melting point: 162-164° C.

Example 2

The above crude DZ2002 (10 g) was suspended in a methanol/water solution (50%, v/v)(50 ml) and heated to dissolve completely, followed by addition of activated carbon (1 g). After the heating and stirring continued for 30 min, the mixture was hot-filtered and the solid was washed with a small amount of hot methanol. The obtained filtrate was disposed in a refrigerator at 4° C., and stored overnight after a small amount of DZ2002 seeds were added therein. After the mixture was filtered, the obtained solid was washed with a small amount of cold anhydrous methanol and dried in vacuo to afford a nearly white crystal (7.3 g) with specific parameters in accordance with the above.

Example 3

The above crude DZ2002 (10 g) was suspended in a water (50 ml) and heated to dissolve completely, followed by addition of activated carbon (1 g). After the heating and stirring continued for 30 min, the mixture was hot-filtered and the solid was washed with a small amount of hot water. The obtained filtrate was disposed in a refrigerator at 4° C., and stored overnight after a small amount of DZ2002 seeds were added therein. After the mixture was filtered, the obtained solid was washed with a small amount of cold water and dried in vacuo to afford a nearly white crystal (6.8 g) with specific parameters in accordance with the above.

The invention claimed is:

1. A method for preparing 4-(6-Amino-purin-9-yl)-2(S)-hydroxy-butyric acid methyl ester, comprising the steps of:

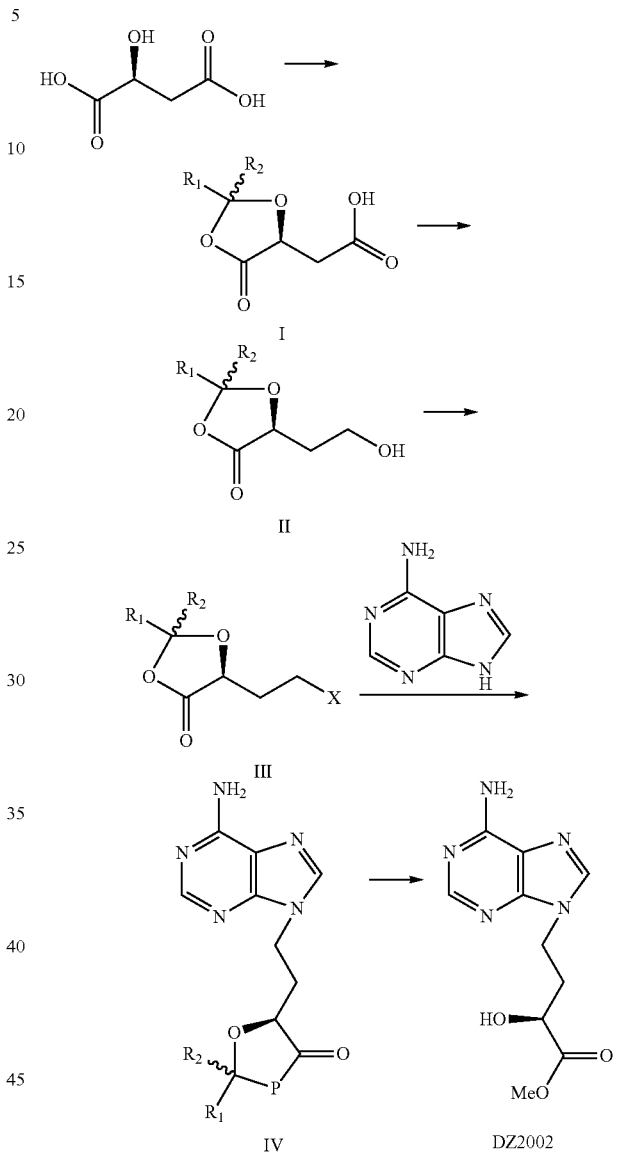

(1) performing a ring-closing reaction by a nucleophilic substitution between L-malic acid and a protective agent, a carbonyl compound having a structure of $R_1COR_2$ or a diol-carbonyl condensation compound thereof, to selectively afford an intermediate I whose 1-carboxyl and 2-hydroxy groups were both protected simultaneously, wherein $R_1$ and $R_2$ are each independently one substituent selected from the group consisting of H, methyl, ethyl, n-propyl, n-butyl, phenyl and p-methoxyphenyl;

(2) reducing the intermediate I obtained from step (1) by a reducing agent selected from the group consisting of a borane agent and a metal hydride to afford an intermediate alcohol II, wherein the 4-carboxyl group of the intermediate I was selectively reduced to the corresponding hydroxyl group;

(3) esterifying the intermediate alcohol II obtained from step (2) by an acyl chloride selected from the group consisting of p-toluenesulfochloride, mesyl chloride, trifluoroacetyl chloride, trichloroacetyl chloride and acetyl chloride in the presence of a base to afford an intermediate III, wherein X is one selected from the group consisting of mesyloxyl, p-toluenesulfonyloxyl, trifluoroacetyloxyl, trichloroacetyloxyl and acetyloxyl; or, halogenating the intermediate alcohol II by a halogenating agent selected from the group consisting of phosphorus tribromide, phosphorus pentabromide, carbon tetrabromide/triphenylphosphine and iodine/triphenylphosphine to afford an intermediate III, wherein X is Br or I;

(4) in the presence of a base and a phase transfer catalyst, performing a nucleophilic substitution between the intermediate III obtained from step (3) and adenine in an appropriate solvent at a suitable temperature to afford an intermediate IV;

(5) deprotecting and methyl-esterifying the intermediate IV obtained from step (4) simultaneously in a methanol system in the presence of an acid or a base to afford 4-(6-Amino-purin-9-yl)-2(S)-hydroxy-butyric acid methyl ester.

2. The method for preparing 4-(6-Amino-purin-9-yl)-2(S)-hydroxy-butyric acid methyl ester according to claim 1, wherein, in step (1), the carbonyl compound is acetone and the diol-carbonyl condensation compound is acetone dimethyl acetal, in the case of $R_1=R_2=$methyl.

3. The method for preparing 4-(6-Amino-purin-9-yl)-2(S)-hydroxy-butyric acid methyl ester according to claim 1, wherein, in step (2), the borane agent is selected from the group consisting of borane, borane-pyridine complex, borane-dimethylthioether complex, borane-tetrahydrofuran complex and borane-ammonia complex, and the metal hydride is selected from the group consisting of $LiAlH_4$, $NaBH_4$, $KBH_4$ and $NaBH_3CN$, wherein in the case of when the reducing agent is a metal hydride, it can be used alone or in combination with a reagent selected from the group consisting of $AlCl_3$, $NiCl_2$, $CeCl_3$, $ZnCl_2$, $LiCl$ and $I_2$.

4. The method for preparing 4-(6-Amino-purin-9-yl)-2(S)-hydroxy-butyric acid methyl ester according to claim 3, wherein the reducing agent of step (2) is selected from the group consisting of borane, borane-pyridine complex, borane-dimethylthioether complex, borane-tetrahydrofuran complex and borane-ammonia complex.

5. The method for preparing 4-(6-Amino-purin-9-yl)-2(S)-hydroxy-butyric acid methyl ester according to claim 1, wherein the base used in step (3) is triethylamine, diisopropylethylamine or pyridine, and the used acyl chloride is toluenesulfochloride or mesyl chloride.

6. The method for preparing 4-(6-Amino-purin-9-yl)-2(S)-hydroxy-butyric acid methyl ester according to claim 1, wherein in the step (4), the reaction is carried out at a temperature in the range of 30° C. to 120° C.; the phase transfer catalyst is selected from the group consisting of tetrabutylammonium bromide, tetrabutylammonium chloride, tetrabutylammonium iodide, 18-crown-6 and polyethylene glycol; the base is an inorganic base selected from the group consisting of sodium hydride, $K_2CO_3$, $Na_2CO_3$, $LiCO_3$, NaOH, KOH and LiOH, or an organic base selected from the group consisting of triethylamine, diisopropylethylamine, pyridine, methylpyridine, n-butyllithium, sec-butyllithium, lithium diisopropylamine, lithium hexamethyldisilazide, sodium hexamethyldisilazide and potassium hexamethyldisilazide; the solvent is a strongly polar non-protonic solvent selected from the group consisting of formamide, DMF, DMA, sulfolane, DMSO, NMP and HMPA, a ketone solvent selected from the group consisting of acetone and butanone, an aromatic solvent selected from the group consisting of benzene and toluene, an ester solvent selected from the group consisting of ethyl acetate and butyl acetate, a chlorohydrocarbon solvent selected from the group consisting of dichloromethane and dichloroethane, or an ether solvent selected from the group consisting of diisopropyl ether, tetrahydrofuran and dioxane.

7. The method for preparing 4-(6-Amino-purin-9-yl)-2(S)-hydroxy-butyric acid methyl ester according to claim 6, wherein in the step (4), the reaction is carried out at a temperature in the range of 40° C. to 60° C.; the phase transfer catalyst may be is 18-crown-6; the base is sodium hydride, $K_2CO_3$ or $Na_2CO_3$; the solvent may be formamide, DMF, DMA, NMP or sulfolane.

8. The method for preparing 4-(6-Amino-purin-9-yl)-2(S)-hydroxy-butyric acid methyl ester according to claim 1, wherein the methanol system of step (5) is a HCl/methanol mixture or a sodium alkoxide/methanol mixture.

9. The method for preparing 4-(6-Amino-purin-9-yl)-2(S)-hydroxy-butyric acid methyl ester according to claim 1, further comprising a step of: purifying 4-(6-Amino-purin-9-yl)-2(S)-hydroxy-butyric acid methyl ester obtained from step (5) via recrystallization from a solvent selected from the group consisting of methanol, ethanol, isopropanol, water and an alcohol-water mixture.

10. The method for preparing 4-(6-Amino-purin-9-yl)-2(S)-hydroxy-butyric acid methyl ester according to claim 1, wherein a racemic 4-(6-Amino-purin-9-yl)-2-hydroxy-butyric acid methyl ester is prepared through the same procedure except replacing the L-malic acid of step (1) with racemic malic acid, followed by a further separation to afford 4-(6-Amino-purin-9-yl)-2(S)-hydroxy-butyric acid methyl ester.

11. A method for preparing 4-(6-Amino-purin-9-yl)-2(S)-hydroxy-butyric acid methyl ester, comprising the steps of:

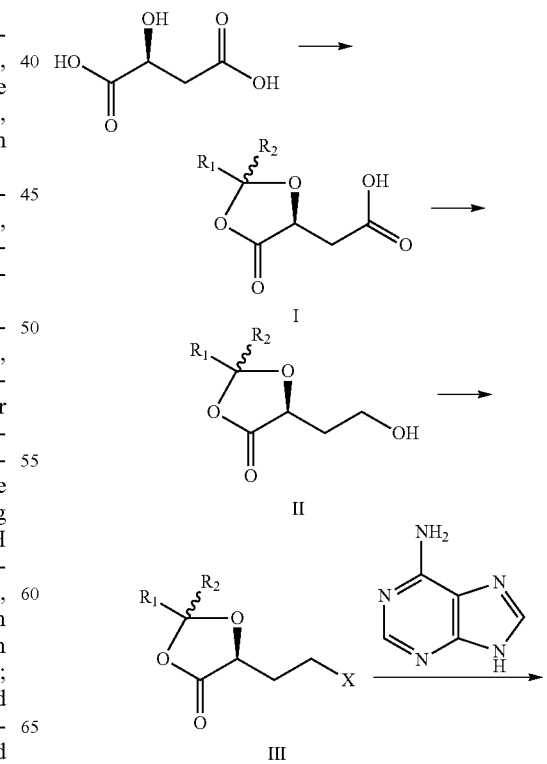

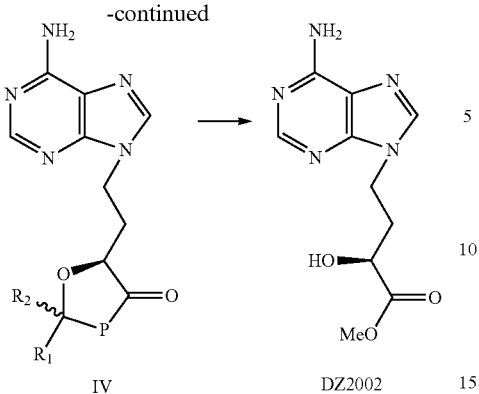

(1) performing a ring-closing reaction by a nucleophilic substitution between L-malic acid and a protective agent, a carbonyl compound having a structure of $R_1COR_2$ or a diol-carbonyl condensation compound thereof, to selectively afford an intermediate I whose 1-carboxyl and 2-hydroxy groups were both protected simultaneously, wherein $R_1$ and $R_2$ are each independently one substituent selected from the group consisting of H, methyl, ethyl, n-propyl, n-butyl, phenyl and p-methoxyphenyl;

(2) reducing the intermediate I obtained from step (1) by a reducing agent selected from the group consisting of a borane agent and a metal hydride to afford an intermediate alcohol II, wherein the 4-carboxyl group of the intermediate I was selectively reduced to the corresponding hydroxyl group;

(3) reacting the intermediate alcohol II obtained from step (2) with adenine via Mitsunobu reaction in the presence of a phosphine agent and diethyl azodiformate or diisopropyl azodiformate to afford an intermediate IV, wherein the phosphine agent is triphenylphosphine or trialkylphosphine, wherein the alkyl is a short chain C1-C4 alkyl; and (4) deprotecting and methyl-esterifying the intermediate IV obtained from step (4) simultaneously in a methanol system in the presence of an acid or a base to afford 4-(6-Amino-purin-9-yl)-2(S)-hydroxy-butyric acid methyl ester.

\* \* \* \* \*